(12) United States Patent
Lewis et al.

(10) Patent No.: US 6,512,144 B1
(45) Date of Patent: Jan. 28, 2003

(54) OXIDATION OF HYDROCARBONS USING CRYSTALLINE MANGANESE (II/III) PHOSPHATE COMPOSITIONS

(75) Inventors: Gregory J. Lewis, Mt. Prospect, IL (US); Paula L. Bogdan, Mt. Prospect, IL (US); Feng Xu, Buffalo Grove, IL (US); Joseph A. Kocal, Glenview, IL (US)

(73) Assignee: UOP LLC, Des Plaines, IL (US)

( * ) Notice: Subject to any disclaimer, the term of this patent is extended or adjusted under 35 U.S.C. 154(b) by 54 days.

(21) Appl. No.: 09/728,536

(22) Filed: Dec. 1, 2000

Related U.S. Application Data

(63) Continuation-in-part of application No. 09/275,202, filed on Mar. 24, 1999, now Pat. No. 6,156,931.

(51) Int. Cl.$^7$ .................. C07C 45/00; C07C 315/00
(52) U.S. Cl. .................. 564/123; 568/27; 568/28; 568/403; 568/471; 568/476; 568/910
(58) Field of Search .................. 423/305, 306, 423/700, 704; 502/208, 213; 568/910, 476, 471, 403, 27, 28; 564/123

(56) References Cited

U.S. PATENT DOCUMENTS 6,156,931 A * 12/2000 Lewis .................. 564/123

OTHER PUBLICATIONS

"Chemistry of the Elements", N.N. Woodward and A. Earnshaw, Pergammon Press, Oxford, pp. 1219–1220, (1984). (No Month).
Yachandra et al., *Science*, 260, 675–679 (1993). (No Month).
S. Bach et al., *Electrochimica Acta*, 36, 1595–1603 (1991). (No Month).
P. LeGoff, et al., *Mat. Res. Bull.*, 31, 63–75 (1996). (No Month).
P. Strobel et al., *Mat. Res. Bull.*, 28, 93–100 (1993). (No Month).
Y. Shen et al., *Science*, 260, 511–515 (1993). (No Month).
Q. Feng et al., *Chem. Mater.*, 7, 148–153 and 1722–1727 (1995). (No Month).
Kampf and Moore, *American Mineralogist*, 61, 1241 (1976). (No Month).
Moore and Ito, *American Mineralogist*, 59, 48 (1974). (No Month).
Roberts et al., *Can. Mineral.*, 27, 451 (1989). (No Month).
Rogers and Brown, *Am. Mineral.*, 64, 169, (1979). (No Month).
Blanchard and Abernathy, *Florida Scientist*, 43, 257 (1980). (No Month).
Schwab, *Soil Sci. Soc. Am. J.*, 53, 1654 (1989). (No Month).
Hawthorne, Z., *Kristallogr.*, 192, 1 (1990). (No Month).
Lightfoot et al. *J. Solid State Chem.*, 73, 325–329 (1988). (No Month).
Lightfoot et al. *J. Solid State Chem.*, 78, 17–22 (1989). (No Month).
Lightfoot et al., *Inorg. Chem.*, 26, 3544–3547 (1987). (No Month).
Aranda et al., *Angew. Chem. Int. Ed. Engl.*, 31, 1090–1092 (1992). (No Month).
Lee et al., *Angew. J. Chem. Soc.* (A) 559–561 (1968). (No Month).
Richtrova et al., *J. Solid State Chem.*, 116, 400–405 (1995). (No Month).
Sarneski et al., *Inorg. Chem.*, 32, 3265–3269 (1993). (No Month).
"Structural Inorganic Chemistry, Fifth Edition," A.F. Wells, Claredon Press, Oxford, pp. 11–15 (1984). (No Month).
Wong and Cheng, *Inorg. Chem.* 31, 1165–1172 (1992). (No Month).

* cited by examiner

Primary Examiner—Wayne A. Langel
(74) Attorney, Agent, or Firm—John G. Tolomei; Frank S. Molinaro

(57) ABSTRACT

Processes for oxidizing hydrocarbons using a new family of crystalline manganese phosphate compositions have been developed. These compositions have an extended network which network can be a one-, two-, or three-dimensional network. The composition has an empirical formula of:

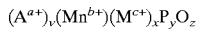

$$(A^{a+})_v(Mn^{b+})(M^{c+})_xP_yO_z$$

where A is a structure directing agent such as an alkali metal, M is a metal such as Al, $Fe^{3+}$ and "b" is the average manganese oxidation state and varies from greater than 2.0 to a maximum of 3.0. Specific oxidation processes are oxidative dehydrodimerization and oxidative dehydrogenation.

13 Claims, No Drawings

OXIDATION OF HYDROCARBONS USING CRYSTALLINE MANGANESE (II/III) PHOSPHATE COMPOSITIONS

CROSS-REFERENCE TO RELATED APPLICATION

This application is a Continuation-in-Part of U.S. application Ser. No. 09/275,202 filed Mar. 24, 1999, U.S. Pat. No. 6,156,931, the contents of which are hereby incorporated by reference.

FIELD OF THE INVENTION

This invention relates to the oxidation of hydrocarbons using a new family of compositions containing at least manganese and phosphate components in an extended network. These compositions can have a one-, two- or three-dimensional network and may be microporous. Further, the average manganese oxidation state varies from greater than 2.0 to 3.0.

BACKGROUND OF THE INVENTION

Manganese occurs in a variety of oxidation states in its oxides, most notably +2, +3, and +4 in nature, and up to +7 in synthetic compounds. Because these different oxidation states are available to manganese, it is possible for manganese containing oxides to engage in oxidation chemistry, converting various compounds to more oxidized and often more useful forms. In order for manganese oxide systems to engage in oxidation chemistry, the average oxidation state of the manganese must be greater than +2, since the +2 oxidation state is the lowest stable oxidation state of Mn in its oxides. Hence, it is the compounds containing some manganese in the +3 and higher oxidation states that can engage in oxidation chemistry and catalysis. Manganese (IV) compounds are well known and are used in a variety of oxidation reactions. For example, manganese dioxide ($MnO_2$) has been used in the manufacture of chlorine gas from hydrogen chloride and the oxidation of aniline to hydroquinone. See "Chemistry of the Elements", N. N. Woodward and A. Earnshaw, Pergammon Press, Oxford, pp. 1219–20 (1984). A molecular manganese-oxo cluster is involved in the oxidation of water to oxygen in the photosynthesis process used by plants. See Yachandra et. al., Science, 260, 675–679 (1993). Because manganese has stable oxidation states of +4, +3 and +2, manganese oxides can be used in batteries.

Manganese oxides can have layered structures or three-dimensional microporous structures. S. Bach et al., Electrochimica Acta, 36, 1595–1603 (1991), P. LeGoff et al., Mat. Res. Bull., 31, 63–75 (1996), P. Strobel et al., Mat Res. Bull., 28, 93–100 (1993), Y. Shen et al., Science, 260, 511–515 (1993). Finally, the ion-exchange properties of manganese oxide compositions have been reported by Q. Feng et al. in Chem. Mater., 7,148–153 and 1722–1727 (1995).

A handful of Mn(III)-containing phosphate compounds are known, some occurring in nature, while others have been synthesized. Among the mineral phosphates containing Mn(III) are:

| | | |
|---|---|---|
| Bermanite | $Mn^{2+}(H_2O)_4[Mn^{3+}_2(OH)_2(PO_4)_2]$ | Kampf and Moore, American Mineralogist, 61, 1241 (1976) |
| Robertsite | $Ca_3Mn^{3+}_4(OH)_6(H_2O)_3[PO_4]_4$ | Moore and Ito, American Mineralogist, 59, 48 (1974) |
| Pararobertsite | $Ca_2Mn^{3+}_3(PO_4)_3O_2 \cdot 3\,H_2O$ | Roberts et al., Can. Mineral, 27, 451 (1989) |
| Mitridatite | $Ca_6(H_2O)_{6[(Fe^{3+}_{8.2}Mn^{3+}_{0.8})O_6(PO_4)_9]} \cdot 3H_2O$ | Rogers and Brown, Am. Mineral, 64, 169 (1979) |
| Purpurite/Heterosite | $(Fe,Mn)PO_4$ | Blanchard and Abernathy, Florida Scientist, 43, 257, (1980) |
| — | $MnPO_4 \cdot 1.5\,H_2O$ | Schwab, Soil Sci. Soc. Am. J, 53, 1654, (1989) |

More information on Mn(III)-containing minerals, especially structure can be found in the review by Hawthorne in Z. Kristallogr., 192, 1 (1990). These materials fall in the classification of octahedral-tetrahedral framework structures, where Mn(III) is always found in octahedral coordination.

There are a number of examples of Mn(III)-containing phosphates that have been prepared by hydrothermal synthesis, e.g., $KMn_2O(PO_4)(HPO_4)$, Lightfoot et. al., J. Solid State Chem., 73, 325–329, (1988), and $NH_4Mn_2O(PO_4)(HPO_4) \cdot H_2O$, Lightfoot et. al., J. Solid State Chem., 78, 17–22, (1989). These materials were obtained via hydrothermal transformation of $Mn_3O_4$ in the presence of $KH_2PO_4$ or $NH_4H_2PO_4$ at 400° C. and 220° C. respectively, relatively harsh conditions. Similarly, $MnPO_4 \cdot H_2O$ was prepared from $Mn_3O_4$, $H_3PO_4$, and water at 200° C., Lightfoot et. al., Inorg. Chem., 26, 3544–3547, (1987). Solid-state ion-exchange of $MnPO_4 \cdot H_2O$ with $LiNO_3$ (4 weeks at 200° C.) led to $LiMn(PO_4)(OH)$, Aranda et. al., Angew. Chem. Int Ed. Engl., 31, 1090–1092, (1992). A number of Mn(III) pyrophosphates, e.g., $NH_4MnP_2O_7$, are known and have found use as pigments, Lee et. al., J. Chem. Soc. (A), 559–561, (1968). Mn(III) has also been substituted for up to one quarter of the $VO^{3+}$ groups in the $VOPO_4 \cdot 2H_2O$ structure, forming $[(Mn(H_2O))_x(VO)_{1-x}PO_4] \cdot 2\,H_2O$, Richtrova et. al., J. Solid State Chem., 116, 400–405, (1995). Finally, an example of a Mn(III)-phosphate complex is the water-soluble dipyridyl complex $[Mn(III)(bpy)(HPO_4)(H_2PO_4)]_x$, Sarneski et. al., Inorg. Chem., 32, 3265–3269, (1993).

In contrast to these references, applicant has synthesized crystalline manganese phosphate compounds which contain Mn(III) and which have an extended network. By extended network is meant that the defining Mn—P—O structural unit of the material repeats itself into at least two adjacent unit cells without termination of bonding, i.e., the material is not molecular. See "Structural Inorganic Chemistry, Fifth Edition," A. F. Wells, Clarendon Press, Oxford, pp. 11–15, (1984). The network can be one-dimensional (a linear chain), two-dimensional (layered) or three-dimensional. The three dimensional network may or may not be a microporous network. By Mn(III)-containing phosphate, it is meant that the average oxidation state of Mn is greater than 2.0 but less than or equal to 3.0, indicating the presence of some Mn(III). These compositions are prepared by trapping the desired manganese oxidation state via titrimetric methods, reduction of a novel manganese(IV) phosphate solution, or hydrothermal transformations of birnessite-like (e.g., $Na_4Mn_{14}O_{27}*xH_2O$) materials, all in the presence of excess phosphate at specific reaction conditions. Besides $MnPO_4*H_2O$, which is ubiquitous in Mn(III) phosphate chemistry and not part of this invention, these methods have not yielded any of the synthesized compounds or mineral structures noted above. This may be due to the mild conditions and the higher reactivity of the reagents employed. In addition, applicant discloses the first manganese(III) and mixed valence Mn(III)/Mn(III) phosphates containing organoammonium cations. Further, applicant has also synthesized metallo manganese phosphates where a portion of the manganese is replaced by a metal such as iron (III), aluminum, gallium, etc.

SUMMARY OF THE INVENTION

This invention relates to hydrocarbon oxidation processes using a crystalline Mn(III)-containing phosphate composition having an extended network. Accordingly, one embodiment of the invention is a process for the oxidation of hydrocarbons comprising contacting a hydrocarbon with a crystalline manganese phosphate composition in the presence of oxygen under oxidation conditions to give an oxidized product, the manganese phosphate composition having an extended network and an empirical composition on an anhydrous basis expressed by an empirical formula of:

$$(A^{a+})_v(Mn^{b+})(M^{c+})_xP_yO_z$$

where A is a structure directing agent which balances the charge on the manganese phosphate framework and is selected from the group consisting of alkali metals, alkaline earth metals (except calcium), hydronium ion, ammonium ion, organoammonium ions, silver, copper (II), zinc (II), nickel (II), mercury (II), cadmium (II) and mixtures thereof, "a" represents a weighted average valence of A and varies from about 1.0 to about 2.0, "v" is the mole ratio of A to Mn and varies from about 0.1 to about 10.0, "b" is the average valence of Mn and has a value of greater than 2 to a maximum of 3, M is a metal selected from the group consisting of Al, $Fe^{3+}$, Ga, $Sn^{4+}$, Ti, $Sb^{5+}$, Ag, Zn, Cu, Ni, Cd, and mixtures thereof, "x" is the mole ratio of M to Mn and varies from 0 to about 3.0, "c" is the weighted average valence of M species and varies from about 1.0 to about 5.0, "y" is the mole ratio of P to Mn and varies from about 0.05 to about 8.0 and "z" is the mole ratio of O to Mn and has a value determined by the equation

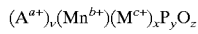

$$z=\tfrac{1}{2}((a\cdot v)+b+(x\cdot c)+(5\cdot y)).$$

This and other objects and embodiments of the invention will become more apparent after a more detailed description of the invention.

DETAILED DESCRIPTION OF THE INVENTION

Oxidation of hydrocarbons involves contacting a hydrocarbon stream with the manganese phosphate compositions described herein at oxidation conditions. Non-limiting examples of these processes include conversion of hydrocarbons to alcohols, ethers, aldehydes, ketones or acid anhydrides; conversion of paraffins to olefins, ammoxidation of paraffins and dimerization of olefins, oxidative dehydrogenation of paraffins, oxidative dehydrodimerization of olefins and ammoxidation of paraffins are commercially more important and will be described in more detail.

When the process is oxidative dehydrodimerization (hereinafter dimerization), the process involves contacting an olefin stream with oxygen and the manganese phosphate composition described hereinafter at dimerization conditions. The manganese phosphate can be used in any configuration, but is usually present as a fixed bed or a radial flow bed. In a fixed bed configuration, the olefin stream can be flowed upflow or downflow although not necessarily with equivalent results. The olefin stream, oxygen and manganese phosphate are contacted for a time sufficient to form dimerized product. In terms of weight hourly space velocity (WHSV) the contact time can vary from about 1 to about 50 $hr^{-1}$. Other dimerization conditions include a temperature of about 350° C. to about 650° C., preferably from about 450° C. to about 600° C., and a pressure from about 0 to about 1000 psig. It is also necessary that oxygen be present during the reaction. The source of oxygen can be either pure oxygen, air, oxygen with an inert diluent gas such as helium or lattice oxygen from the manganese phosphate. The amount of oxygen present is such that the ratio of olefin to oxygen ($O_2$) varies from about 1.5:1 to about 10:1 preferably from 3:1 to 8:1.

The oxidative dehydrodimerization can also be carried out using the lattice oxygen of manganese phosphate as the source of oxygen. This approach can often yield higher selectivities to dimers than can be obtained with the oxygen co-fed process described above. In this mode of operation, manganese is reduced when exposed to the olefin feed. When a portion of the available lattice oxygen is used a regeneration step is carried out to restore the oxidation capability of the manganese phosphate. The manganese phosphate composition can be cycled between oxidation and regeneration numerous times.

For oxidative dehydrogenation, the manganese phosphate composition can be used in the same manner as described above for dimerization. Contacting of the paraffin with oxygen and the catalyst is done for a sufficient time to dehydrogenate the paraffin. Accordingly, the GHSV varies from about 100 to about 10,000 $hr^{-1}$ and preferably from about 300 to about 2000 $hr^{-1}$. Other dehydrogenation conditions include a temperature of about 250° C. to about 650° C. and a pressure of about 1 to about 45 psig. The source of oxygen can be any of the ones enumerated above and is present in a ratio of paraffin:$O_2$ of about 1:10 to about 5:1.

Ammoxidation of paraffins is carried out in a similar manner to the processes above with the following differences. The process involves reacting a paraffin with ammonia in the presence of a manganese phosphate composition. Ammoxidation conditions include a GHSV of about 100 to about 5,000 $hr^1$, a temperature of about 300° C. to about 520° C. and a pressure of about 1 to about 45 psig. Finally, the ammonia: paraffin ratio varies from about 1:10 to about 5:1.

Ammoxidation of paraffins is carried out in a similar manner to the processes described above with the following differences. The process involves reacting a paraffin with ammonia in the presence of a manganese phosphate composition. Ammoxidation conditions include a GHSV of about 100 to about 5,000 $hr^{-1}$, a temperature of about 300° C. to about 520° C. and a pressure of about 1 to about 45 psig. Finally, the ammonia: paraffin ration varies from about 1:10 to about 5:1. Surprisingly, in certain instances, this process resulted in the conversion of ammonia to nitrous oxide $N_2O$. Nitrous oxide is a valuable oxidant and specialty chemical.

The manganese phosphate compositions used in the processes described above have a chemical composition on an anhydrous basis expressed by the empirical formula:

$$(A^{a+})_v(Mn^{b+})(M^{c+})_xP_yO_z$$

where A is a templating agent selected from the group consisting of alkali metals, alkaline earth metals (except calcium), hydronium ion, ammonium ion, organoammonium ions, silver, copper (II), zinc (II), nickel (II), mercury (II), cadmium (II), and mixtures thereof, "a" represents a weighted average valence of A and varies from about 1.0 to about 2.0, "v" is the mole ratio of A to Mn and varies from about 0.1 to about 10, "b" is the average valence of Mn and has a value of greater than 2 to a maximum of 3, M is a metal selected from the group consisting of Al, $Fe^{3+}$, Ga, $Sn^{4+}$, Ti, $Sb^{5+}$, Ag, Zn, Cu, Ni, Cd, and mixtures thereof, "x" is the mole ratio of M to Mn and varies from 0.0 to about 3.0, "c" is the weighted average valence of M and varies from about 1.0 to about 5.0, "y" is the mole ratio of P to Mn and varies from about 0.05 to about 8.0 and "z" is the mole ratio of O to Mn and has a value determined by the equation $$z=\tfrac{1}{2}((a\cdot v)+b+(x\cdot c)+(5\cdot y)).$$

The alkali metals include lithium, sodium, potassium, rubidium and cesium, while the alkaline earth metals include magnesium, strontium and barium. Illustrative examples of organoammonium ions include but are not limited to methylammonium, ethylenediammonium, propylammonium, and hexylammonium.

When A is one structure directing agent, the weighted average valence is the valence of the one structure directing agent. However, when more than one templating agent is used, the total amount of:

$$A_v^{a+}=A_i^{a_i+}+A_j^{a_j+}+A_k^{a_k+}+\ldots$$

and the weighted average valence "a" is defined by:

$$a=\frac{a_i\cdot i+a_j\cdot j+a_k\cdot k+\ldots}{i+j+k+\ldots}$$

The weighted average valence of manganese ("b") is dependent on the amount of $Mn^{2+}$ and $Mn_{3+}$ present in the composition. Thus, if the total amount of manganese "w" is defined by w=p+q, where "p" is the mole fraction of $Mn^{2+}$, "q" is the mole fraction of $Mn^{3+}$ then the average valence:

$$b=\frac{2p+3q}{p+q}.$$

Similarly, when two or more metals (M) are present, the amount of each metal is defined by:

$$M_x^{c+}=M_\alpha^{c_\alpha+}+M_\beta^{c_\beta+}+M_\gamma^{c_\gamma+}+\ldots$$

and the average valence C is determined by the equation:

$$C=\frac{C_\alpha\cdot\alpha+C_\beta\cdot\beta+C_\gamma\cdot\gamma+\ldots}{\alpha+\beta+\gamma+\ldots}$$

The crystalline compositions of the invention are characterized in that they have an extended network. By extended network is meant that the defining Mn—P—O structural unit of the material repeats itself into at least two adjacent unit cells without termination of bonding, i.e., the material is not molecular. See "Structural Inorganic Chemistry, Fifth Edition," A. F. Wells, Clarendon Press, Oxford, pp. 11–15, (1984). The compositions can have a one-dimensional network which is a linear chain, a two-dimensional network which is a layered network or a three-dimensional network which is either a microporous framework structure or a non-microporous framework structure.

The instant manganese phosphate compositions are prepared by hydrothermal crystallization of a reaction mixture prepared by combining reactive sources of phosphorus, manganese, optionally one M metal, at least one structure directing agent (A) plus water. Specific examples of the phosphorus sources which can be used in this invention are orthophosphoric acid, pyrophosphoric acid, alkali phosphates and sodium metaphosphate. The manganese source can be either a high oxidation state salt such as $KMnO_4$, $NaMnO_4$, $CsMnO_4$, $NH_4MnO_4$, $Mg(MnO_4)_2$ and $Ba(MnO_4)_2$. Other sources of manganese are birnessite and buserite. Birnessite, e.g., $Na_4Mn_{14}O_{27}\cdot 9H_2O$, and a more hydrated form called buserite are layered manganese oxides which contain charge balancing cations and water between the layers. The oxidation state of Mn in these materials is about +3.3 to about +3.7. These materials can be prepared in a variety of cation forms such as $Li^+$, $Na^+$, $K^+$, $Rb^+$, $Cs^+$ and $NH_{4+}$ where the cations are present between the layers. These cations can be partially or totally exchanged with other cations such as $Mg^{2+}$, $Sr^{2+}$, $Ba^{2+}$, $Zn^{2+}$, $Cu^{2+}$, $Ag^+$, $Ni^{2+}$, $Cd^{2+}$, $Hg^{2+}$, or mixtures thereof.

The layers can also be expanded with organoammonium cations via an initial treatment in acid followed by a treatment with an amine. A variety of amines including propylamine may be employed for the purpose of creating reactive expanded birnessites for use in making the new manganese phosphates of this invention. More details on preparing expanded birnessites can be found in Wong and Cheng, Inorg. Chem., 31, 1165–1172. These sources of manganese oxide are very reactive and easily transformed to other structures. The Mg-exchanged version of bimessite can be structurally transformed hydrothermally to form the microporous manganese oxide todorokite, Y. Shen et al., Science, 260, 511–515 (1993). In this invention, the various forms of birnessite and buserite are hydrothermally transformed in the presence of excess phosphate, where phosphate can engage in bonding with the manganese oxide while structural transformations occur. The oxidation state of Mn in the resulting compounds is usually +3 or less, depending on pH, temperature, and the nature of A.

Manganese sources can also be any layered manganese oxide pillared with a variety of organoammonium cations such as methylammonium, ethylammonium, propylammonium, butylammonium, hexylammonium, ethylenediammonium, tetramethylammonium and mixtures thereof. Additionally, 1,4 diazabicyclo[2.2.2] octane (DABCO) alone or in combination with organoammonium cations such as enumerated above can also be used. Combinations of ammonium cation and any organoammonium cations (and/or DABCO) can also be used. The series of layered manganese (IV)-containing phosphates, examples of which are described as NaMnP-1a and NaMnP-1b in U.S. Pat. No. 5,780,003, (which is incorporated by reference) in their various metal substituted (for manganese) and cation exchanged forms, also can be used as sources of manganese for preparing the manganese phosphates of this invention.

Finally, it is preferred to use a special manganese solution prepared from NaMnO$_4$ and H$_3$PO$_4$ whose preparation is described in detail in example 1 of U.S. Pat. No. 5,780,003, which is incorporated by reference. This phosphate-stabilized manganese solution has a composition represented by the empirical formula $$NaMnO_4{:}rH_3PO_4{:}sR{:}uH_2O$$

where R is a reductant selected from the group consisting of H$_2$C$_2$O$_4$, Na$_2$C$_2$O$_4$, NaHCO$_2$ and Mn(NO$_3$)$_2$.6H$_2$O, "r" has a value of about 3.0 to about 30, "s" is the mole ratio of R:NaMnO$_4$ sufficient to reduce the manganese oxidation state to a value of greater than 3 to about 4 and varies from about 1.5 to about 4, and "u" is the moles of water and varies from about 25 to about 1000 in order to vary the manganese concentration from 0.1 wt. % to about 5 wt. %. The preferred form of this solution contains 1 wt. % manganese and is called the "1% Solution" in the rest of this application. The advantage to this solution is that it is stable over a long period of time, i.e., months, and facilitates the preparation of the instant compositions by adding a templating agent, such as an organoammonium salt or amine, or alternatively an alkali metal or alkaline earth in combination with a suitable portion of reductant to this solution and heating the resultant mixture. This solution is especially convenient with the organoammonium cations and amines because these structure directing agents react uncontrollably with other soluble high oxidation state Mn salts, such as the permanganates (MnO$_4$$^-$) listed above. Substituent metals, such as Al, Fe, and others may also be introduced into this solution and aged before the appropriate crystallization inducing agents are added. Using this solution and suitable reductants, it is possible to prepare a variety of Mn (III) and mixed valence Mn(III)/Mn(II) phosphates. Examples of reductants include but are not limited to amines and organoammonium species, which also serves as the charge-balancing species for the manganese phosphate framework. In this process, the original amine or organoammonium species will be partially oxidized, often resulting in the formation of fragments of the original amine or organoammonium species. Hence, the charge-balancing species for the manganese phosphate framework may be one of these fragments or a mixture thereof and different from the original amine or organoammonium species introduced into the synthesis mixture. Because of this, the elemental analyses will often yield non-integral carbon/nitrogen ratios for the organoammonium groups. Other reductants include inorganic or organoammonium formates and oxalates and various chloride salts.

Another method to prepare the manganese phosphates of this invention is via the hydrothermal treatment of MnPO$_4$*H$_2$O or its metal-substituted forms in alkaline solutions. The alkaline solutions may be formed by alkaline hydroxides, organoammonium hydroxides, ammonium hydroxide, or a variety of amines. The manganese(III) phosphate MnPO$_4$*H2O used for these reactions is easily prepared by reacting excess concentrated phosphoric acid with nitric acid and Mn (NO$_3$)$_2$.4H$_2$O and isolating the MnPO$_4$.H$_2$O product.

Yet another way to make the novel manganese phosphates of this invention is to use a "trapping" method in which the desired manganese oxidation state is generated in the presence of excess phosphate via a redox reaction. For example, a soluble permanganate MnO$_4$$^-$ is dissolved in a solution containing excess phosphoric acid and is reduced using a reducing agent such as formate or oxalate salts. The purpose of the excess phosphate is to avoid the formation of insoluble manganese oxides in the +3 and +4 oxidation states and insure that a manganese phosphate forms instead. Hence, as the typically insoluble oxidation states of manganese are formed, they are "trapped" and stabilized by the excess phosphate.

The non-manganese sources must be chosen in a manner such that the source, the digestion temperature, and the pH will yield manganese phosphates with average oxidation states greater than 2+, but less than or equal to 3.0. Not every source of structure directing agent enumerated in the following list is compatible with every source of manganese with respect to attaining the desired manganese oxidation state. The source of the alkali or alkaline earth metals structure directing agents include the acetate, nitrate, carbonate, and hydroxide compounds. Specific examples include sodium chloride, sodium nitrate, sodium acetate, sodium carbonate, sodium hydroxide, lithium chloride, lithium nitrate, lithium carbonate, lithium hydroxide, rubidium chloride, rubidium nitrate, rubidium carbonate, rubidium hydroxide, cesium chloride, cesium nitrate, cesium carbonate, cesium hydroxide, potassium chloride, potassium nitrate, potassium carbonate, potassium hydroxide, magnesium chloride, magnesium nitrate, magnesium carbonate, magnesium hydroxide, barium chloride, barium nitrate, barium carbonate, barium hydroxide, strontium chloride, strontium nitrate, strontium carbonate and strontium hydroxide. Sources of organoammonium ions include methylamine, hexylamine, propylamine, and ethylenediamine. The organoammonium cation is generated in situ via protonation. Organoammonium cations may also be quaternized, such as tetramethylammonium and tetraethylammonium, employed as either hydroxides or chlorides. Finally, sources of the M metal include the nitrate salts of the metals as well as TiCl$_3$, NaSbF$_6$, and SnCl$_4$.

Generally, the hydrothermal process used to prepare the manganese phosphate of this invention involves forming a reaction mixture which has the formula:

$$dAO_{a/2}{:}MnO_{m/2}{:}eMO_{c/2}{:}fP_2O_5{:}gB{:}hR{:}tH_2O$$

where B is a mineralizer, R is a reductant, "d" ranges from about 0.5 to about 20, "e" ranges from 0 to about 3.0, "f" ranges from about 0.5 to about 15, "g" ranges from 0 to about 2, "h" ranges from 0 to about 5, "t" ranges from about 25 to about 1000, and "m" ranges from about 3 to about 7. Examples of the mineralizer B include HF and NaF, while examples of the reductant R include NaHCO$_2$, H$_2$C$_2$O$_4$, and Na$_2$C$_2$O$_4$.

It also is necessary to adjust the pH of the mixture to a value of about 2.0 to about 12.0. The pH of the mixture can be controlled by addition of a base such as NaOH, NH$_4$OH, amines, etc.

Having formed the reaction mixture, it is next reacted at a temperature of about 50° C. to about 175° C. for a period of about 12 hours to about 240 hours. The reaction is carried out under atmospheric pressure or the reaction vessel may be sealed and the reaction run at autogenous pressure. In a preferred method the phosphorus source and the manganese source is the "1% solution", the temperature is from about 70° C. to about 100° C. and the time required to crystallize the product is from about 16 hours to about 120 hours.

It should be pointed out that not all the enumerated structure directing agents can provide all the various structures possible in the generic class of extended network manganese phosphate compositions. The relationship of specific structure directing agents to individual products is apparent from the illustrative examples set forth herein.

The oxidation state of manganese in the manganese phosphates described here is one of the characterizing properties of these new materials. The measurement of the oxidation state of manganese was carried out according to a variation of the oxalate method given in Piper et. al., *Geochimica et Cosmochimica Acta*, 48, 1237–1247, (1984). The Mn-containing sample is reduced to $Mn^{2+}$ when it is digested at 85° C. in a dilute sulfuric acid solution containing a known excess of sodium oxalate, the reducing agent. The solution is divided into two portions, one of which is analyzed for total Mn. In the second portion, the excess oxalate not consumed by the reduction of the sample is back-titrated with standardized $KMnO_4$, allowing the determination of the amount of oxalate consumed by the sample. The average oxidation state of manganese is then determined from the amount of oxalate consumed and the concentration of Mn in the sample.

In the examples which follow elemental analyses were conducted on air dried samples. Analysis was carried out for all elements except oxygen. Organoammonium and ammonium salts were determined by high temperature oxidative pyrolysis, yielding C, H, and N analyses. Because of the oxidizing nature of the reaction mixture used to prepare the compositions of this invention, all the metals (other than Mn) were assumed to be in their highest oxidation state, e.g., $Fe^{3+}$ or $Ti^{4+}$. Therefore, the oxygen stoichiometry was determined from the known oxygen requirements of all of the elements including the measured oxidation state of the manganese.

The structure of the manganese phosphates of this invention was determined by x-ray analysis. The x-ray patterns presented in the following examples were obtained using standard x-ray powder diffraction techniques. The radiation source was a high-intensity, x-ray tube operated at 45 kV and 35 ma. The diffraction pattern from the copper K-alpha radiation was obtained by appropriate computer based techniques. Flat compressed powder samples were continuously scanned at 2° (2θ) per minute from 2° to 70° (2θ). Interplanar spacings (d) in Angstrom units were obtained from the position of the diffraction peaks expressed as θ where θ is the Bragg angle as observed from digitized data. Intensities were determined from the integrated area of diffraction peaks after subtracting background, "$I_o$" being the intensity of the strongest line or peak, and "I" being the intensity of each of the other peaks.

As will be understood by those skilled in the art the determination of the parameter 2θ is subject to both human and mechanical error, which in combination can impose an uncertainty of about ±0.4° on each reported value of 2θ. This uncertainty is, of course, also manifested in the reported values of the d-spacings, which are calculated from the 2θ values. This imprecision is general throughout the art and is not sufficient to preclude the differentiation of the present crystalline materials from each other and from the compositions of the prior art. In some of the x-ray patterns reported, the relative intensities of the d-spacings are indicated by the notations vs, s, m, and w which represent very strong, strong, medium, and weak, respectively. In terms of 100× $I/I_o$, the above designations are defined as:

w=0–15; m=15–60; s=60–80 and vs=80–100.

In certain instances the purity of a synthesized product may be assessed with reference to its x-ray powder diffraction pattern. Thus, for example, if a sample is stated to be pure, it is intended only that the x-ray pattern of the sample is free of lines attributable to crystalline impurities, not that there are no amorphous materials present.

To allow for ready reference, the different structure types in the following examples have been given arbitrary numbers such as MnP-1. Thus $NH_4MnP$-7 and RbMnP-7 have the same structure, i.e., structure type 7. Additionally, variations have been observed in compositions having the same structure types. These have been designated by a letter after the number, e.g., MnP-14a and MnP-14b. The crystalline compositions of the instant invention may be characterized by their X-ray powder diffraction patterns and such may have one of the X-ray patterns containing the d-spacings and intensities set forth in the following tables. The intensities are the relative intensities as stated above.

TABLE A

MnP-4

| d(Å) | I |
|---|---|
| 7.5–8.3 | vs |
| 7.0–7.6 | w |
| 4.9–5.5 | w - m |
| 4.6–5.2 | w |
| 2.8–3.4 | w |
| 2.5–3.1 | w - m |

TABLE B

MnP-5

| d(Å) | I |
|---|---|
| 10.0–10.8 | vs |
| 5.0–5.7 | w |
| 4.3–4.9 | w |
| 3.0–3.6 | w - m |
| 2.5–3.1 | w - m |
| 1.7–2.3 | w |

TABLE C

MnP-7

| d(Å) | I |
|---|---|
| 10.3–11.1 | vs |
| 5.1–5.7 | w |
| 4.3–4.9 | w |
| 3.3–3.9 | w - m |
| 2.5–3.1 | w - s |
| 1.8–2.4 | w |

TABLE D

MnP-8

| d(Å) | I |
|---|---|
| 10.5–11.3 | vs |
| 5.6–6.4 | w |
| 5.0–5.6 | w |
| 4.0–4.6 | w |
| 3.0–3.6 | w |
| 2.0–2.5 | w |

TABLE E

MnP-9

| d(Å) | I |
|---|---|
| 14.0–15.5 | vs |
| 7.0–7.8 | w |
| 5.2–6.0 | w |
| 3.0–3.6 | w |
| 2.5–3.1 | w |

TABLE F

MnP-10

| d(Å) | I |
|---|---|
| 8.3–9.1 | vs |
| 5.2–6.0 | w |
| 4.0–4.6 | w |
| 3.0–3.6 | w |
| 2.5–3.1 | m |
| 1.9–2.5 | w |

TABLE G

MnP-11

| d(Å) | I |
|---|---|
| 10.7–11.5 | vs |
| 5.2–5.6 | w |
| 3.4–4.0 | w |
| 3.0–3.5 | w |
| 2.5–3.0 | w |
| 2.0–2.4 | w |

TABLE H

MnP-12

| D(Å) | I |
|---|---|
| 10.3–11.1 | vs |
| 5.2–6.0 | m |
| 3.0–3.5 | m |
| 2.5–3.0 | m |
| 2.2–2.7 | w |
| 1.4–1.8 | w |

TABLE I

MnP-13

| d(Å) | I |
|---|---|
| 8.1–8.9 | vs |
| 5.3–5.9 | w - m |
| 4.4–5.0 | w |
| 3.0–3.4 | w |
| 2.5–3.0 | m |
| 1.9–2.3 | w |

TABLE J

MnP-14

| d(Å) | I |
|---|---|
| 8.5–9.3 | vs |
| 5.3–5.9 | m |
| 4.3–4.9 | w |
| 3.0–3.4 | m |
| 2.5–3.0 | m |
| 2.0–2.4 | m |

TABLE K

MnP-15

| d(Å) | I |
|---|---|
| 10.3–11.1 | vs |
| 5.4–6.0 | m |
| 4.7–5.3 | w - m |
| 3.0–3.5 | w - m |
| 2.6–3.0 | m |
| 1.4–1.8 | w |

TABLE L

MnP-16

| d(Å) | I |
|---|---|
| 10.5–11.3 | vs |
| 4.7–5.3 | w - m |
| 3.7–4.1 | w |
| 3.0–3.5 | m - s |
| 2.5–3.0 | m |
| 1.4–1.8 | w |

TABLE M

MnP-17

| d(Å) | I |
|---|---|
| 21.0–23.0 | vs |
| 14.0–15.6 | m |
| 10.6–11.4 | w |
| 7.0–7.8 | w |
| 4.9–5.5 | w |
| 3.9–4.3 | w |

TABLE N

MnP-18

| d(Å) | I |
|---|---|
| 12.5–13.3 | vs |
| 5.3–5.9 | w - m |
| 3.0–3.5 | w - m |
| 2.5–3.0 | m |
| 1.4–1.8 | w |

TABLE O

| | MnP-19 | |
|---|---|---|
| d(Å) | | I |
| 9.3–10.1 | | vs |
| 5.3–5.9 | | w - m |
| 3.0–3.5 | | m |
| 2.6–3.1 | | m - s |
| 1.9–2.3 | | w |
| 1.4–1.8 | | w |

TABLE P

| | MnP-20 | |
|---|---|---|
| d(Å) | | I |
| 13.5–14.3 | | vs |
| 6.7–7.3 | | w |
| 5.3–5.8 | | w |
| 4.4–5.0 | | w |
| 3.0–3.5 | | w |
| 2.5–3.0 | | w |

TABLE Q

| | MnP-21 | |
|---|---|---|
| d(Å) | | I |
| 11.0–11.8 | | vs |
| 5.3–5.9 | | w |
| 4.3–4.9 | | w |
| 3.0–3.5 | | w |
| 2.5–3.0 | | w - m |
| 2.0–2.5 | | w |

TABLE R

| | MnP-22 | |
|---|---|---|
| d(Å) | | I |
| 9.5–10.3 | | vs |
| 5.0–5.6 | | w |
| 3.8–4.4 | | w |
| 3.0–3.5 | | m |
| 2.6–2.9 | | m |
| 2.3–2.7 | | m |

TABLE S

| | MnP-23 | |
|---|---|---|
| d(Å) | | I |
| 18.0–19.8 | | m |
| 9.0–9.8 | | vs |
| 6.0–6.5 | | w |
| 5.4–5.9 | | w |
| 4.4–5.0 | | w |
| 2.4–2.9 | | w |

TABLE T

| | MnP-24 | |
|---|---|---|
| d(Å) | | I |
| 10.2–11.0 | | vs |
| 6.4–6.7 | | w |
| 3.6–4.1 | | w |
| 3.3–3.8 | | m |
| 3.0–3.5 | | w - m |
| 2.5–3.0 | | w - m |

In order to more fully illustrate the variety of species to be derived from the instant invention, the following examples are set forth. It is to be understood that the examples are only by way of illustration and are not intended as an undue limitation on the broad scope of the invention as set forth in the appended claims.

EXAMPLE 1

Na, K, and $NH_4$ Birnessites were prepared in the following manner. In a 5 liter teflon liner, 120 g $MnSO_4 \cdot H_2O$ were dissolved in 1200 g $H_2O$. Oxygen was bubbled vigorously through the stirred solution for 45 minutes. Separately, 330 g NaOH (544 g 85% KOH, or 600 g $NH_4OH$(29% $NH_3$)) was dissolved in 1200 g $H_2O$ and chilled to about 7° C. in an ice bath. After the manganese sulfate solution was thoroughly purged with $O_2$, the chilled hydroxide solution was added. The resulting mixture was purged with $O_2$ for 10 hours while it was stirred. The brown-black to black product suspensions were isolated by filtration and washed thoroughly with de-ionized water. The product was stored in air tight bottles so the materials would retain their moisture. This method was adapted from Golden et al, Clay and Clay Minerals, 35(4), 271–280, (1987).

EXAMPLE 2

In a teflon beaker, 62.62 g $NaH_2PO_4$ was dissolved in 219 g de-ionized $H_2O$. The solution was placed under a high speed mixer and 50.0 g of a moist sodium birnessite(16.7% Mn) was added as chunks. The mixture was homogenized for 40 minutes, at which time the pH was 5.1. The mixture was poured into teflon-lined autoclaves and digested for 83 hours at 150° C. at autogenous pressure. The product, a greenish solid, was filtered, washed thoroughly with distilled water, and dried at room temperature. This product was designated MnP-4.

Titrimetric analysis of the product yielded an average manganese oxidation state of 3.03, which is within experimental error of 3.0. Combined with the elemental analysis, this yields an empirical formula of $Na_{0.95}Mn_{1.00}P_{0.96}O_{4.38}$. Characteristic lines observed in the x-ray diffraction pattern are shown in Table 1.

TABLE 1

| 2θ | d(Å) | I |
|---|---|---|
| 11.13 | 7.94 | vs |
| 12.17 | 7.27 | w |
| 17.10 | 5.18 | w |
| 17.79 | 4.99 | w |
| 18.97 | 4.68 | w |
| 21.56 | 4.12 | w |
| 22.23 | 4.00 | w |
| 23.19 | 3.84 | w |
| 26.03 | 3.42 | w |

TABLE 1-continued

| 2θ | d(Å) | I |
|---|---|---|
| 27.62 | 3.23 | w |
| 28.76 | 3.10 | w |
| 29.98 | 2.98 | w |
| 31.64 | 2.83 | w |
| 32.34 | 2.77 | w |
| 33.55 | 2.67 | w |
| 33.96 | 2.64 | w |
| 34.67 | 2.59 | w |
| 36.77 | 2.44 | w |
| 37.82 | 2.38 | w |
| 42.64 | 2.12 | w |

EXAMPLE 3

A teflon beaker was charged with 492 g de-ionized water, in which 109.68g $KH_2PO_4$ was subsequently dissolved. The mixture was placed under a high speed mixer and to it there were added 100.0 g of moist K-birnessite (7.4% Mn) as chunks, allowing the mixer to break up the chunks as the addition proceeded. Over the course of an hour, the brown suspension became very thick. The pH of the reaction mixture was 5.34 before it was placed into teflon-lined autoclaves for digestion. The digestion was carried out at 150° C. at autogenous pressure for 136 hr. The yellow brown product was filtered and washed with de-ionized water. This material was designated MnP-5.

Table 2 shows the characteristic XRD lines of MnP-5. More complete characterization of MnP-5 prepared via a different route is given in example 26.

TABLE 2

| 2θ | d(Å) | I |
|---|---|---|
| 8.49 | 10.41 | vs |
| 15.82 | 5.60 | w |
| 16.58 | 5.34 | w |
| 17.02 | 5.20 | w |
| 19.28 | 4.60 | w |
| 21.16 | 4.19 | w |
| 25.64 | 3.47 | w |
| 27.12 | 3.29 | m |
| 31.55 | 2.83 | w |
| 31.95 | 2.80 | w |
| 32.20 | 2.78 | w |
| 32.67 | 2.74 | w |
| 33.49 | 2.67 | w |
| 34.43 | 2.60 | w |
| 34.56 | 2.59 | w |
| 35.30 | 2.54 | w |
| 40.72 | 2.21 | w |
| 42.07 | 2.15 | w |
| 43.41 | 2.08 | w |
| 45.05 | 2.01 | w |
| 55.88 | 1.64 | w |

EXAMPLE 4

In a teflon beaker, 14.42 g $(NH_4)_2HPO_4$ was dissolved in 78.7 g de-ionized water. The solution was homogenized with a high speed mixer as chunks of $NH_4$-birnessite (8% Mn), 25.0 g, were added. The mixture was homogenized for 20 minutes at which point the pH was 8.71. The mixture was split among 9 teflon-lined autoclaves, which were digested for 1, 2, and 8 days at temperatures of 125° C., 150° C., and 170° C. at autogenous pressure. The material digested for 8 days at 170° C. yielded some red-brown plate crystals, which were filtered from the colorless mother liquor and washed with de-ionized water. The red-brown crystals were designated MnP-6.

A single crystal study was undertaken on the red-brown crystals of MnP-3. The diffractometer employed was the Enraf-Nonius CAD4 using CuKα radiation (λ=1.54178 Å). The crystal was indexed on a monoclinic unit cell of dimensions a=4.524 Å, b=6.254 Å, c=8.513 and β=96.78°. Data was collected over the index ranges of $-5 \leq h \leq 0$, $-7 \leq k \leq 0$, and $-10 \leq l \leq 10$, resulting in 611 reflections, of which 517 were observed (F>4.0 F(F)). The space group was determined to be $P2_1/m$. The structure was solved via direct methods using SHELXTL PLUS program and refined using full-matrix least squares procedures. The R-indices, which indicate the agreement between the observed data and the calculated model, were R=4.78% and $R_w$=7.73%. A valence bond analysis of the manganese coordination environment, using the procedure and the parameters of Breese and O'Keefe (Acta Cryst (1991), B47, 192–197), indicated a situation consistent with a +3 oxidation state for manganese. The oxygen atoms bonded to manganese and not phosphorus, O4 in the table below, are part of a hydroxyl group. The empirical formula indicated by the structure is $NH_4Mn(OH)PO_4$, a Mn(III) phosphate. The positions of the atoms are given in the Table 3 below.

TABLE 3

| Atom | x | y | z |
|---|---|---|---|
| Mn | 0.50000 | 0 | 0.50000 |
| P | 0.90505 | 0.25000 | 0.29206 |
| O1 | 0.72689 | 0.04680 | 0.32671 |
| O2 | 1.19468 | 0.25000 | 0.40700 |
| O3 | 0.94972 | 0.25000 | 0.12066 |
| O4 | 0.68821 | 0.25000 | 0.61077 |
| N | 0.39749 | 0.25000 | -0.07318 |

EXAMPLE 5

In a teflon beaker, 27.00 g $(NH_4)_2HPO_4$ was dissolved in 141.20 g de-ionized water and the resulting solution placed under a high speed mixer. $NH_4$-birnessite, 35.00 g, was then added to the reaction mixture with vigorous stirring. The reaction mixture was homogenized for 30 minutes, after which time the pH was 8.76. The thick suspension was transferred to teflon-lined autoclaves, which were digested at either 150° C. or 170° C. for 22 hours at autogenous pressure. The light brown products were filtered, washed thoroughly with distilled water and air dried. These products are designated $NH_4MnP$-7.

Both digestion temperatures gave the same XRD pattern. Titrimetric analysis revealed the average manganese oxidation state to be 2.99. Combined with the elemental analysis, this yields an empirical formula of $(NH_4)_{0.90}Mn_{1.00}P_{0.92}O_{4.25}$. Characteristic lines in the x-ray diffraction pattern are given in Table 4 below.

TABLE 4

| 2θ | d(Å) | I |
|---|---|---|
| 8.22 | 10.75 | vs |
| 16.48 | 5.38 | w |
| 19.04 | 4.66 | w |
| 24.80 | 3.59 | w |
| 27.12 | 3.29 | w |
| 31.56 | 2.83 | w |
| 31.86 | 2.81 | w |

TABLE 4-continued

| 2θ | d(Å) | I |
|---|---|---|
| 33.28 | 2.69 | w |
| 34.39 | 2.61 | w |
| 39.52 | 2.28 | w |
| 41.92 | 2.15 | w |
| 44.28 | 2.05 | w |
| 50.78 | 1.80 | w |
| 55.85 | 1.65 | w |
| 56.59 | 1.63 | w |

EXAMPLE 6

In a teflon beaker, 27.38 g $H_3PO_4$ (85%) was diluted with 200 g de-ionized water. This solution was partially neutralized with 39.1 g RbOH (50%) solution. This solution was placed under a mechanical mixer and 40.4 g of Rb-Birnessite (8.8% Mn) was added with vigorous stirring. The reaction mixture was homogenized for 1 hour after which time the pH was 6.1. The resulting brown suspension was transferred to teflon-lined autoclaves and digested at 125° C., 150° C., or 175° C. for a week at autogenous pressure. The brown products were filtered from a colorless mother liquor, washed thoroughly with distilled water and air-dried.

The samples that were digested at 125° C. and 150° C. yielded the product that is designated RbMnP-7. The average manganese oxidation state was not measured for this sample, but is believed to be about 3.0 or slightly less by analogy to the Na, K, and $NH_4$ examples (2, 3, 4, 5, 27). Characteristic lines in the x-ray diffraction pattern are given in Table 5 below.

TABLE 5

| 2θ | d(Å) | I |
|---|---|---|
| 8.24 | 10.72 | vs |
| 15.74 | 5.63 | w |
| 18.92 | 4.69 | w |
| 20.76 | 4.27 | w |
| 24.89 | 3.57 | m |
| 27.02 | 3.30 | m |
| 31.40 | 2.85 | m |
| 31.82 | 2.81 | s |
| 33.31 | 2.69 | w |
| 34.40 | 2.61 | w |
| 37.05 | 2.42 | w |
| 37.69 | 2.27 | w |
| 44.29 | 2.04 | w |
| 47.73 | 1.90 | w |
| 48.57 | 1.87 | w |
| 50.84 | 1.79 | m |
| 55.64 | 1.65 | w |
| 55.78 | 1.65 | w |
| 56.48 | 1.63 | w |
| 65.49 | 1.42 | w |

EXAMPLE 7

It is well known that Na Birnessite can be exchanged with other metal cations such as $Mg^{2+}$ or $Cu^{2+}$ (See Golden et al, Clays and Clay Minerals, 35(4), 271–280, (1987). This can usually be accomplished by stirring Na-Birnessite in a large excess of a 0.5 M solutions of the metal nitrate. The resulting $M^{n+}$-exchanged birnessite is also a suitable material for preparing the manganese phosphates of this invention.

Phosphoric acid (85%), 115.1 g, was diluted with 224.4 g de-ionized water. Solid $Mg(OH)_2$, 29.17 g, was added to the solution with stirring. The resulting mixture was placed under a high speed mixer and 49.0 g Mg-Bimessite was added. The mixture was homogenized for 2 hours before it was divided among 9 teflon-lined autoclaves. The reaction mixtures were digested at autogenous pressures at temperatures of 125° C., 150° C., and 175° C. for time periods of 42 hr, 96 hr, and 165 hr. The products were isolated by filtration, washed thoroughly with de-ionized water, and dried at room temperature.

The 150° C. and 175° C. conditions led to the formation of a new material. The 175° C. condition gave complete conversion of the birnessite after 96 hr, but also gave rise to a slight $MnPO_4*H_2O$ impurity, which was observed in the XRD. The oxidation state of manganese in this material was not measured, but is expected to be about 3.0 or slightly less because of the similarity of the conditions to those employed in the alkali metal examples. The elemental analysis yielded the formulation $Mg_{1.42}Mn_{1.00}P_{2.38}O_x$. The new material is designated MnP-8. Characteristic lines in the x-ray diffraction pattern is presented in Table 6 below.

TABLE 6

| 2θ | d(Å) | I |
|---|---|---|
| 8.11 | 10.89 | vs |
| 14.57 | 6.07 | w |
| 16.23 | 5.46 | w |
| 16.67 | 5.31 | w |
| 20.80 | 4.27 | w |
| 21.89 | 4.06 | w |
| 22.12 | 4.01 | w |
| 23.57 | 3.77 | w |
| 24.45 | 3.64 | w |
| 27.57 | 3.23 | w |
| 29.17 | 3.06 | w |
| 30.53 | 2.93 | w |
| 31.19 | 2.87 | w |
| 33.18 | 2.70 | w |
| 33.72 | 2.66 | w |
| 36.65 | 2.45 | w |
| 39.92 | 2.26 | w |

EXAMPLE 8

This example shows that birnessites that are pillared with organoammonium cations also serve as suitable precursors to $Mn^{3+}$-containing phosphates. The starting material for this example was propylammonium birnessite, which was prepared by acid exchanging Na- Birnessite with 1 M $HNO_3$ solution for 24 hr. The acid exchanged material is then treated with a 3 M propylamine solution for 2–5 days, forming a colloidal suspension. The suspension is precipitated by adjusting the pH to less than pH 6 via the addition of acetic acid solution. The resulting propylammonium birnessite is washed thoroughly with de-ionized water and dried at room temperature.

Phosphoric acid (85%), 104.1 g, was added to 164.1 g de-ionized water in a teflon beaker. Propylamine (98%), 114.78 g, was slowly added to the solution with stirring. The solution was homogenized employing a mechanical mixer and propylammonium birnessite, 20.0 g, was added. The reaction mixture was stirred vigorously for 45 minutes, after which time it was separated into six portions, each of which was placed in a teflon-lined autoclave. The reaction mixtures were digested for 1 week at 70° and 100° C., 4 and 7 days at 125° C., and 2 and 4 days at 150° C. The products were isolated by filtration, washed thoroughly with de-ionized water, and dried at room temperature.

The mild conditions of the 70° C. preparation were the most favorable for the preparation of product designated MnP-9. Titrimetric analysis revealed the average Mn oxidation state to be 2.49. Combined with the elemental analysis, this leads to the empirical formula $(NC_{2.5}H_9)_{0.49}Mn_{1.00}P_{0.76}O_{3.39}$. Characteristic lines in the diffraction pattern are given in Table 7 below.

TABLE 7

| 2θ | d(Å) | I |
|---|---|---|
| 6.06 | 14.57 | vs |
| 12.26 | 7.21 | w |
| 15.72 | 5.63 | w |
| 27.38 | 3.25 | w |
| 31.80 | 2.81 | w |
| 37.99 | 2.37 | w |
| 42.48 | 2.13 | w |
| 56.85 | 1.62 | w |

EXAMPLE 9

A solution containing a manganese (IV) phosphate at a level of 1 wt. % Mn (0.2M in Mn) with an average oxidation state of 3.85 was prepared as follows and is herein referred to as the "1% Solution." The preparation of the 1% solution is the same as that described in U.S. Pat. No. 5,780,003 which is incorporated by reference.

In a 12 liter round bottom flask equipped with a mechanical stirrer and a dropping funnel there was added 5800 g of distilled water followed by 1802 g of concentrated (85.7 wt. %) $H_3PO_4$ and 250 g of $NaMnO_4 \cdot H_2O$ to give a dark purple solution. In a separate container 159.44 g of $NaHCO_2$ was dissolved in 576 g distilled water. This solution was placed in a dropping funnel and added dropwise to the stirring $NaMnO_4/H_3PO_4$ solution. The resultant mixture became a black-brown color over the course of the addition. Upon completion of the addition, the mixture was stirred for three to five days and then filtered on a buchner funnel. The filtered solution was analyzed and found to contain 1.0±0.1 wt. % Mn and the manganese had an average oxidation state of 3.85. This solution was identified as "1% Solution" in the examples below.

EXAMPLE 10

A 600 g portion of the 1% Solution was placed in a teflon beaker. As this solution was stirred, 60.6 g propylamine (98%) was added dropwise. When the addition was completed, the mixture was homogenized with a high speed mixer for an hour. The resulting dark brown thin suspension was then placed in a teflon bottle and digested at 70° C. for 3 days. A red-brown solid was isolated by filtration, washed thoroughly with de-ionized water, and dried at room temperature. This material was designated MnP-10.

Titrimetric analysis of the sample determined the average Mn oxidation state to be 2.68. Combined with elemental analysis, the empirical formula $(NC_{1.43}H_{6.68})_{0.09}Na_{0.69}Mn_{1.00}P_{0.99}O_{4.20}$ was obtained. Table 8 gives characteristic lines of the x-ray diffraction pattern for MnP-10.

TABLE 8

| 2θ | d(Å) | I |
|---|---|---|
| 10.16 | 8.70 | vs |
| 15.68 | 5.65 | w |
| 20.33 | 4.36 | w |
| 20.56 | 4.32 | w |
| 27.44 | 3.25 | w |
| 30.95 | 2.89 | m |
| 31.70 | 2.82 | m |
| 32.06 | 2.79 | m |
| 41.45 | 2.18 | w |
| 56.42 | 1.63 | w |

EXAMPLE 11

A 200 g portion of the 1% Solution was placed in a teflon beaker. While stirring, 26.70 g methylamine (40% aqueous solution) were added in a dropwise manner. When the addition was completed, the resulting reaction mixture was homogenized with a high speed mixer for an hour. The black-brown thin suspension was placed in a teflon bottle and digested at 70° C. for 3 days at autogenous pressure. The brown-red product was isolated via filtration, washed with de-ionized water, and dried at room temperature. This material was designated MnP-11.

Titrimetric analysis revealed the average oxidation state of manganese to be 2.86 in this material. Combined with the elemental analysis, the empirical formula $(H_3NCH_3)_{0.27}Na_{0.42}Mn_{1.00}P_{0.96}O_{4.17}$ was obtained. Characteristic lines in the x-diffraction pattern are given in Table 9 below.

TABLE 9

| 2θ | d(Å) | I |
|---|---|---|
| 7.96 | 11.10 | vs |
| 15.83 | 5.60 | w |
| 24.15 | 3.68 | w |
| 27.49 | 3.24 | w |
| 32.06 | 2.79 | w |
| 40.69 | 2.22 | w |
| 56.78 | 1.62 | w |

EXAMPLE 12

A 200.5 g portion of the 1% Solution was placed in a teflon beaker and stirred. Propylamine (98%), 48.92 g, was then added dropwise to the 1% Solution. Upon completion of the addition, the reaction mixture was homogenized with a high speed mixer for an hour. The brown suspension was placed in teflon-lined autoclaves and digested at temperatures of 70° C., 100° C., and 125° C. for a duration of 2 or 4 days. The solid products were isolated via filtration, washed with de-ionized water, and dried at room temperature.

The conditions employing the temperature of 70° C. and a time of 2 days was most favorable and this product was designated MnP-12. Titrimetric analysis revealed the average oxidation state of the manganese to be 2.99. Combined with the elemental analysis, this yields the empirical formula $Na_{0.32}(NC_3H_{10})_{0.33}Mn_{1.00}PO_{0.60}O_{3.33}$. Characteristic lines in the XRD pattern are given in Table 10 below.

TABLE 10

| 2θ | d(Å) | I |
|---|---|---|
| 8.23 | 10.74 | vs |
| 15.83 | 5.60 | m |
| 16.48 | 5.38 | w |

TABLE 10-continued

| 2θ | d(Å) | I |
|---|---|---|
| 27.50 | 3.24 | m |
| 31.98 | 2.80 | m |
| 32.69 | 2.74 | m |
| 36.63 | 2.45 | w |
| 41.57 | 2.17 | w |
| 56.72 | 1.62 | w |
| 65.79 | 1.42 | w |

EXAMPLE 13

A 200.0 g portion of the 1% Solution was placed in a teflon beaker and stirred. Tetraethylammonium hydroxide (40%), 150.99 g, was added dropwise to the 1% solution. When the addition was completed, the reaction mixture was homogenized with a high speed mixer for an hour. The thin brown gel/suspension was distributed among six teflon bottles which were digested at temperatures of 70° C., and 100° C. for durations of 1, 2, and 4 days. The solid products were isolated via filtration, washed with de-ionized water, and dried at room temperature.

The samples digested at 100° C. all yielded the same material according to x-ray diffraction data and are designated MnP-13. Elemental analyses showed that the materials digested for 1 and 2 days at 100° C. contained a Mn/P ratio of 6/5. Titrimetric analysis for the sample digested for 2 days revealed an average manganese oxidation state of 2.76. The elemental analysis suggested the empirical formula $Na_{0.87}(NC_{2.4}H_{8.8})_{0.04}Mn_{1.00}P_{0.83}O_{3.92}$ for the 1 day sample. lines in the x-ray diffraction pattern are given in Table 11 below.

TABLE 11

| 2θ | d(Å) | I |
|---|---|---|
| 10.38 | 8.51 | vs |
| 15.83 | 5.59 | m |
| 18.94 | 4.68 | w |
| 20.78 | 4.27 | w |
| 27.52 | 3.24 | w |
| 31.33 | 2.85 | m |
| 31.89 | 2.80 | w |
| 33.53 | 2.67 | m |
| 34.68 | 2.58 | w |
| 35.26 | 2.54 | w |
| 38.28 | 2.35 | w |
| 42.16 | 2.14 | w |
| 45.21 | 2.00 | w |
| 53.64 | 1.71 | w |
| 56.60 | 1.62 | w |

EXAMPLE 14

A 200.1 g portion of the 1% Solution was placed in a teflon beaker. A 25% NaOH solution was prepared of which 86.8 g was added dropwise to the stirring 1% Solution to adjust the pH to 6.5. Then 2.22 g ethylenediamine was added to the reaction mixture. The reaction mixture was homogenized with a high speed mixer for an hour. The thin brown suspension was divided into four teflon bottles which were digested at 70° C. and 100° C. for time periods of 1 and 4 days. The solid products were isolated by filtration, washed with de-ionized water, and dried at room temperature.

The most favorable reaction condition was digestion at 100° C. for 24 hr yielding the product that has been designated MnP-14a. Titrimetric analysis revealed an average manganese oxidation state of 2.56. Combined with the elemental analysis this yields an empirical formula of $(H_3NCH_2CH_2NH_3)_{0.32}Na_{0.74}Mn_{1.00}P_{0.98}O_{4.42}$. Characteristic lines in the x-ray diffraction pattern are given in Table 12 below.

TABLE 12

| 2θ | D(Å) | I |
|---|---|---|
| 9.88 | 8.94 | vs |
| 15.67 | 5.65 | m |
| 15.91 | 5.57 | m |
| 19.38 | 4.58 | w |
| 20.13 | 4.41 | w |
| 27.58 | 3.23 | m |
| 30.32 | 2.95 | m |
| 31.64 | 2.83 | m |
| 32.15 | 2.78 | m |
| 32.61 | 2.74 | m |
| 33.19 | 2.70 | w |
| 34.45 | 2.60 | w |
| 40.78 | 2.21 | m |
| 51.05 | 1.79 | w |
| 57.00 | 1.61 | w |

EXAMPLE 15

A 200.0 g portion of the 1% Solution was placed in a teflon beaker. Separately, 12.19 g NaOH was dissolved in 38.6 g de-ionized water. The resulting solution was added dropwise to the 1% Solution with stirring, resulting in the formation of a brown suspension. An ethylenediamine solution was then prepared by diluting 4.38 g ethylenediamine with 4.1 g de-ionized water. This solution was added dropwise to the reaction mixture and homogenized for 45 minutes with a high speed mixer. Solid $CsNO_3$, 14.19 g, was added at this time and the mixture was homogenized for an additional 2 hr. The final reaction mixture was divided among six teflon bottles which were digested at 70° C. and 100° C. for periods of 24 hr, 53 hr, and 90 hr. The solid products were isolated via filtration, washed with de-ionized water, and dried at room temperature.

The conditions yielding the sample of interest were a digestion temperature of 100° C. for a period of 24 hr. This material was designated MnP-14b. Titrimetric analysis revealed an average manganese oxidation state of 2.87. Combined with the elemental analysis, this yields an empirical formula of $(H_3NCH_2CH_2NH_3)_{0.15}Cs_{0.03}Na_{0.71}Mn_{1.00}P_{0.99}O_{4.43}$. Characteristic lines in the x-ray diffraction pattern are given in Table 13 below.

TABLE 13

| 2θ | d(Å) | I |
|---|---|---|
| 9.78 | 9.04 | vs |
| 15.65 | 5.66 | m |
| 15.88 | 5.57 | m |
| 19.32 | 4.59 | w |
| 27.19 | 3.28 | m |
| 27.57 | 3.23 | m |
| 30.29 | 2.95 | m |
| 31.64 | 2.83 | m |
| 32.14 | 2.78 | m |
| 32.57 | 2.75 | w |
| 33.07 | 2.71 | w |
| 33.22 | 2.69 | w |
| 34.42 | 2.60 | w |
| 40.70 | 2.21 | m |
| 57.15 | 1.61 | w |

EXAMPLE 16

A 200.2 g portion of the 1% Solution was placed in a teflon beaker. The pH was adjusted to 6.5 by adding 84.28 g of a 25 wt. % NaOH solution dropwise with stirring. Then 6.33 g N,N,N',N'-tetramethyl-1,6-hexanediamine was added. This mixture was homogenized with a high speed mixer for an hour. The thin brown gel was divided among four teflon bottles, which were digested at 70° C. and 100° C. for periods of 1 and 4 days. The solid products were isolated by filtration, washed with de-ionized water, and dried at room temperature.

The optimum condition for this reaction was determined to be the mild condition of 70° C. for 1 day. The product was designated MnP-15a. Titrimetric analysis revealed an average manganese oxidation state of 2.77. Combined with the elemental analysis, this yields an empirical formula of $Na_{0.79}Mn_{1.00}P_{0.88}O_{3.98}$. Characteristic lines in the x-ray diffraction pattern are given in Table 14 below.

TABLE 14

| 2θ | d(Å) | I |
|---|---|---|
| 8.24 | 10.72 | vs |
| 15.64 | 5.66 | m |
| 16.48 | 5.37 | w |
| 17.66 | 5.02 | m |
| 27.21 | 3.27 | m |
| 31.51 | 2.84 | m |
| 31.94 | 2.80 | w |
| 32.61 | 2.74 | m |
| 33.25 | 2.69 | w |
| 35.74 | 2.51 | w |
| 42.05 | 2.15 | w |
| 56.06 | 1.64 | w |
| 56.76 | 1.62 | w |

EXAMPLE 17

A 271.3 g portion of the 1% Solution was placed in a teflon beaker. The pH was adjusted to 5.1 via the dropwise addition of 78.9 g of a 25 wt. % NaOH solution. When the addition was completed, hexylamine, 10.0 g, was added. Upon addition of the hexylamine, the reaction mixture became a light brown suspension. The reaction mixture was homogenized with a high speed mixer for 30 minutes. The suspension was divided among five teflon bottles and digested at 25° C. (with stirring) for 4 days, at 50° C. for 2 and 4 days, and at 70° C. for 2 and 4 days. The solid products were isolated by filtration, washed with de-ionized water, and dried at room temperature.

The 50° C. and 70° C. conditions were found to be favorable conditions, with the optimum being a digestion temperature of 50° C. for a duration of 4 days. This material is very similar to and is considered to be another form of MnP-15, and is designated MnP-15b. Titrimetric analysis revealed the average manganese oxidation state to be 2.90. Combined with the elemental analysis, this yields an empirical formula of $Na0.63Mn_{1.00}P_{0.78}O_{3.72}$. Characteristic lines in the x-ray diffraction pattern are shown in Table 15.

TABLE 15

| 2θ | d(Å) | I |
|---|---|---|
| 8.20 | 10.78 | vs |
| 15.61 | 5.68 | m |
| 16.47 | 5.38 | w |
| 17.60 | 5.04 | w |
| 27.19 | 3.28 | w |
| 31.51 | 2.84 | m |
| 32.58 | 2.75 | m |
| 35.70 | 2.51 | w |

TABLE 15-continued

| 2θ | d(Å) | I |
|---|---|---|
| 41.99 | 2.15 | w |
| 56.06 | 1.64 | w |

EXAMPLE 18

A 200.0 g portion of the 1% Solution was placed in a teflon beaker. Separately, 13.1 g NaOH was dissolved in 39.3 g de-ionized water to make a 25% NaOH solution. This solution was added dropwise to the brown-black 1% Solution and the reaction mixture reached a pH of 4.5 when the addition was completed. A 0.55 g portion of ethylenediamine was diluted with 4.50 g de-ionized water while a 1.25 g portion of phosphoric acid (85%) was similarly diluted with 5.40 g de-ionized water. The ethylenediamine solution was then neutralized by the phosphoric acid solution. At this point, 21.27 g solid $CsNO_3$ was added to the partially neutralized 1% Solution and the resulting mixture was stirred for 15 minutes. After this time, the ethylenediamine/phosphoric acid solution was poured into the reaction mixture and then stirred for two hours. The reaction mixture was divided among four teflon bottles which were digested at 50° C. for 74 hrs. and 146 hrs. and 70° C. for periods of 26 hrs. and 49 hrs. The solid products were isolated by filtration, washed with de-ionized water, and dried at room temperature.

The optimal conditions were a digestion temperature of 70° C. for a period of 49 hrs. The resulting material was designated MnP-16. Titrimetric analysis revealed the average manganese oxidation state to be 3.05. The value of 3.0 is assigned to the average manganese oxidation state since the value of 3.05 is within the experimental error. Combined with the elemental analysis, this yields the empirical formula $Na_{0.65}Cs_{0.30}Mn_{1.0}P_{0.99}O_{4.45}$. Characteristic lines in the x-ray diffraction pattern are given in Table 16 below.

TABLE 16

| 2θ | d(Å) | I |
|---|---|---|
| 8.12 | 10.88 | vs |
| 17.58 | 5.04 | m |
| 22.57 | 3.94 | w |
| 24.68 | 3.60 | w |
| 27.17 | 3.28 | s |
| 29.12 | 3.06 | w |
| 31.49 | 2.84 | m |
| 31.83 | 2.81 | m |
| 32.55 | 2.75 | m |
| 40.43 | 2.23 | w |
| 44.44 | 2.04 | w |
| 45.35 | 2.00 | w |
| 46.10 | 1.97 | w |
| 56.02 | 1.64 | m |

EXAMPLE 19

A 1000.0 g portion of the 1% Solution was placed in a teflon beaker. Hexylamine (98%), 105.78 g, was added dropwise to the 1% Solution to bring the pH to 4.77. The reaction mixture was homogenized with a high speed stirrer for an hour. The resulting suspension was placed in a teflon bottle and digested at 70° C. for 3 days. The solid products were isolated via filtration, washed with de-ionized water, and dried at room temperature. This brown fluffy solid was designated MnP-17.

Titrimetric analysis of the product revealed an average manganese oxidation state of 3.00. Combined with the elemental analysis, this yields an empirical formula of $(NC_6H_{16})_{1.11}Na_{0.09}Mn_{1.0}P_{1.29}O_{5.33}$ for this material. Characteristic lines in the x-ray diffraction pattern are given in Table 17 below.

TABLE 17

| $2\theta$ | d(Å) | I |
|---|---|---|
| 4.01 | 22.01 | vs |
| 5.96 | 14.81 | m |
| 8.05 | 10.97 | w |
| 11.93 | 7.41 | w |
| 17.00 | 5.21 | w |
| 17.90 | 4.95 | w |
| 21.67 | 4.10 | w |
| 23.94 | 3.71 | w |
| 24.33 | 3.66 | w |
| 27.49 | 3.24 | w |
| 31.68 | 2.82 | w |
| 56.32 | 1.63 | w |

EXAMPLE 20

A 400.2 g portion of the 1% Solution was placed in a teflon beaker. This was followed by the dropwise addition of 86.37 g propylamine (98%) to the 1% Solution with stirring, adjusting the pH to about 9.0. The resulting mixture was homogenized with a high speed mixer for one hour. The final reaction mixture was placed in a teflon bottle and digested at 70° C. for 3 days. The solid products were isolated via filtration, washed with de-ionized water, and dried at room temperature. This product was designated MnP-18.

Titrimetric analysis revealed the average manganese oxidation state to be 2.98. Combined with the elemental analysis, this yields an empirical formula of $(NC_{2.07}H_{8.14})_{0.50}Na_{0.62}Mn_{1.0}P_{1.02}O_{4.60}$. The lines in the x-ray diffraction pattern were broad for this material. Characteristic lines in the x-ray diffraction pattern are given in Table 18 below.

TABLE 18

| $2\theta$ | d(Å) | I |
|---|---|---|
| 6.85 | 12.89 | vs |
| 9.74 | 9.07 | m |
| 15.96 | 5.55 | m |
| 27.54 | 3.24 | m |
| 32.07 | 2.79 | m |
| 42.53 | 2.12 | w |
| 56.85 | 1.62 | w |

EXAMPLE 21

A 200.2 g portion of the 1% Solution was placed in a teflon beaker. As this solution was stirred, 11.30 g ethylenediamine was added in a dropwise fashion, bringing the pH to 4.75. The reaction mixture was homogenized with a high speed mixer for an hour. The thin brown suspension was then distributed among six teflon bottles which were digested at 70° C. and 100° C. for time periods of 1, 2, and 4 days. The solid products were isolated by filtration, washed with de-ionized water, and dried at room temperature.

The conditions required to prepare the sample of interest were a digestion temperature of 70° C. for a duration of 2 days. The resulting material is designated MnP-19. Titrimetric analysis revealed an average oxidation state of 2.63. Combined with the elemental analysis, this yields the empirical formula $(H_3NCH_2CH_2NH_3)_{0.34}Na_{0.23}Mn_{1.0}P_{1.01}O_{4.30}$. Characteristic lines in the x-ray diffraction pattern are given in Table 19 below.

TABLE 19

| $2\theta$ | d(Å) | I |
|---|---|---|
| 9.12 | 9.69 | vs |
| 15.64 | 5.66 | m |
| 16.32 | 5.43 | m |
| 27.14 | 3.28 | m |
| 31.40 | 2.85 | m |
| 32.06 | 2.79 | m |
| 33.04 | 2.71 | m |
| 42.04 | 2.15 | w |
| 55.96 | 1.64 | m |

EXAMPLE 22

A 200.1 g portion of the 1% Solution was placed in a beaker. Solid 1,4 diazabicyclo [2.2.2] octane (DABCO) (97%), 65.03 g, was slowly added to the reaction mixture to bring the pH to about 7.0. When the addition was completed, the reaction mixture was homogenized with a high speed stirrer for an hour. The final reaction mixture was distributed among 6 teflon bottles and digested at temperatures of 70° C. and 100° C. for time periods of 1, 2, and 4 days. The solid products were isolated via filtration, washed with de-ionized water, and dried at room temperature The optimal conditions for preparing this material, designated MnP-20, were a digestion temperature of 70° C. for a period of 4 days. A titrimetric analysis of the average manganese oxidation state was not performed on this sample, but is expected to be 3.0 or slightly less as seen in other preparations in which DABCO was the reductant (See examples 23 and 24). Elemental analysis indicated the empirical formula to be $(DABCOH_2^{2+})_{0.30}Na_{0.31}Mn_{1.0}P_{1.08}O_x$. Characteristic lines in the x-ray diffraction pattern are:

TABLE 20

| $2\theta$ | d(Å) | I |
|---|---|---|
| 6.36 | 13.88 | vs |
| 12.55 | 7.05 | w |
| 16.01 | 5.53 | w |
| 17.85 | 4.97 | w |
| 18.81 | 4.72 | w |
| 25.04 | 3.55 | w |
| 27.55 | 3.24 | w |
| 31.96 | 2.80 | w |
| 37.94 | 2.37 | w |
| 56.72 | 1.62 | w |

EXAMPLE 23

A 300.0 g portion of the 1% Solution was placed in a teflon beaker. Separately, 17.47 g NaOH was dissolved in 52.42 g de-ionized water and placed in a dropping funnel. The hydroxide solution was added dropwise to the stirring 1% Solution, bringing the pH to 5.75. A DABCO solution (3.06 g DABCO diluted with 12.5 g de-ionized water) was treated with a phosphoric acid solution (3.15 g 85% phosphoric acid diluted with 7.0 g de-ionized water) and the resulting mixture was added to the 1% Solution. After stirring for a half hour, 16.56 g $KNO_3$ was added as a solid. The reaction mixture was allowed to stir for an additional hour before it was divided among four teflon bottles. The samples were digested at temperatures of 75° C. for 1 and 2 days and at 100° C. for 18 hrs and 39 hrs. The solid products were isolated via filtration, washed with de-ionized water, and dried at room temperature.

The optimal conditions yielding the material of interest, designated MnP-21, were a digestion temperature of 75° C. for a duration of 24 hrs. Titrimetric analysis revealed the average manganese oxidation state to be 2.81. Combined with the elemental analysis, this yields an empirical formula of $Na_{0.71}K_{0.35}Mn_{1.0}P_{1.10}O_{4.69}$. Characteristic lines in the x-ray diffraction pattern are given in Table 21 below.

TABLE 21

| 2θ | d(Å) | I |
|---|---|---|
| 7.79 | 11.34 | vs |
| 15.66 | 5.65 | w |
| 16.12 | 5.50 | w |
| 19.37 | 4.58 | w |
| 19.98 | 4.44 | w |
| 23.61 | 3.77 | w |
| 27.51 | 3.24 | w |
| 28.46 | 3.13 | w |
| 30.51 | 2.93 | w |
| 31.84 | 2.81 | w |
| 32.63 | 2.74 | w |
| 33.06 | 2.71 | w |
| 34.63 | 2.59 | w |
| 36.24 | 2.48 | w |
| 39.87 | 2.26 | w |
| 46.34 | 1.96 | w |
| 52.96 | 1.72 | w |
| 56.85 | 1.62 | w |

EXAMPLE 24

A 330.0 g portion of the 1% Solution was placed in a teflon beaker. Separately, 19.22 g NaOH was dissolved in 57.66 g de-ionized water and the resulting solution was added dropwise to the 1% Solution with stirring. Next, a DABCO/phosphoric acid solution was prepared by dissolving 3.37 g DABCO with 19.0 g de-ionized water, diluting 3.47 g phosphoric acid (85%) with 8.0 g de-ionized water, and mixing the two solutions together. After the NaOH addition to the 1% solution was completed and the mixture allowed to stir, the DABCO/phosphoric acid solution was added in a single pour. The reaction mixture was allowed to stir before adding 35.12 g $CsNO_3$ as a solid. The brown suspension was further homogenized before it was distributed among four teflon bottles which were digested at temperatures of 75° C. for 1 and 2 days and 100° C. for periods of 18 hrs and 39 hrs. The solid products were isolated by filtration, washed with de-ionized water, and dried at room temperature.

The product of interest was prepared via digestion at 100° C. for 39 hrs. This material was designated MnP-22. Titrimetric analysis revealed the average manganese oxidation state to be 2.80. Combined with the elemental analysis, this yields an empirical formula of $Na_{0.59}Cs_{0.29}Mn_{1.00}P_{1.00}O_{4.35}$. Characteristic lines in the XRD pattern are shown in Table 22 below.

TABLE 22

| 2θ | d(Å) | I |
|---|---|---|
| 8.91 | 9.91 | vs |
| 15.81 | 5.60 | w |
| 16.61 | 5.33 | w |

TABLE 22-continued

| 2θ | d(Å) | I |
|---|---|---|
| 19.10 | 4.64 | w |
| 21.54 | 4.12 | w |
| 25.38 | 3.51 | w |
| 27.09 | 3.29 | m |
| 30.19 | 2.96 | w |
| 31.55 | 2.83 | m |
| 32.04 | 2.79 | w |
| 32.72 | 2.73 | w |
| 36.35 | 2.47 | m |
| 42.83 | 2.11 | w |
| 43.83 | 2.06 | w |
| 45.80 | 1.98 | w |
| 46.56 | 1.95 | w |
| 55.92 | 1.64 | w |

EXAMPLE 25

In a 4-liter beaker, 377.02 g NaOH was dissolved in 1450 g de-ionized water. Once this solution cooled a little, 1151.6 g phosphoric acid (85%) was slowly added to this solution with stirring. The resulting solution was again allowed to cool; the pH was 2.68. Then 120.01 g $NaMnO_4*H_2O$ was added and the resulting mixture was heated to 50° C. with a hotplate. Then 103.1 g $NaHCO_2$ was dissolved in 242.8 g de-ionized water and the resulting solution placed in a dropping funnel. This solution was added dropwise to the reaction mixture as it was maintained at 50° C. After the addition was completed, the reaction mixture was maintained at 70° C. while it was stirred for an hour. The resulting dark brown mixture was placed in a 5-liter teflon-lined autoclave and digested at 150° C. for 69 hrs. The solid product was isolated via filtration, washed with de-ionized water, and dried in air.

The green-brown solid product had the x-ray diffraction pattern characteristic of MnP-4, which is disclosed in example 1. Assuming the same oxidation state, the elemental analysis yields the empirical formula $Na_{1.01}Mn_{1.00}P_{1.02}O_{4.55}$, very similar to that observed in example 1. Characteristic lines observed in the x-ray diffraction pattern are given in Table 23 below.

TABLE 23

| 2θ | d(Å) | I |
|---|---|---|
| 10.98 | 8.05 | vs |
| 12.02 | 7.35 | w |
| 16.94 | 5.23 | m |
| 17.63 | 5.03 | w |
| 18.80 | 4.72 | w |
| 21.41 | 4.15 | w |
| 22.07 | 4.02 | w |
| 23.04 | 3.86 | w |
| 25.88 | 3.44 | w |
| 27.47 | 3.24 | w |
| 28.62 | 3.12 | m |
| 29.25 | 3.05 | w |
| 29.82 | 2.99 | w |
| 31.50 | 2.84 | w |
| 32.18 | 2.78 | m |
| 33.38 | 2.68 | w |
| 33.82 | 2.65 | w |
| 34.35 | 2.61 | w |
| 34.55 | 2.59 | m |
| 36.63 | 2.45 | w |
| 37.70 | 2.38 | w |
| 43.64 | 2.07 | w |

EXAMPLE 26

Into a 4-liter beaker containing 1400 g de-ionized water, 865.3 g phosphoric acid (85%) was added with stirring.

Then 120 g $KMnO_4$ was added and allowed to dissolve. Separately, 143.52 g $KHCO_2$ was dissolved in 206.5 g de-ionized water and placed in a dropping funnel. The formate solution was added dropwise to the reaction mixture over a period of 30 minutes. The resulting suspension was allowed to stir for an hour. A KOH solution was prepared by dissolving 486.3 g KOH in 451.25 g de-ionized water. This solution was then slowly added to the reaction mixture, which was further homogenized for an hour with a high speed mixer. The final reaction mixture was placed in a 5-liter teflon-lined autoclave and digested at 150° C. at autogenous pressure for 5 days. The solid products were isolated via filtration, washed with de-ionized water, and dried at room temperature.

The product was identified as MnP-5 by XRD, the same product disclosed in example 2 above. Titrimetric analysis of the product yielded an average manganese oxidation state of 2.82. Combined with the elemental analysis, this yields an empirical formula of $K_{0.95}Mn_{1.0}P_{0.99}O_{4.36}$. Characteristic lines in the x-ray diffraction pattern are given in Table 24 below.

TABLE 24

| 2θ | d(Å) | I |
|---|---|---|
| 8.49 | 10.41 | vs |
| 15.80 | 5.60 | w |
| 16.56 | 5.35 | w |
| 17.01 | 5.21 | w |
| 19.27 | 4.60 | w |
| 21.08 | 4.21 | w |
| 25.63 | 3.47 | w |
| 27.09 | 3.29 | w |
| 31.51 | 2.84 | w |
| 31.91 | 2.80 | w |
| 32.16 | 2.78 | w |
| 32.65 | 2.74 | w |
| 33.46 | 2.68 | w |
| 34.40 | 2.60 | w |
| 35.26 | 2.54 | w |
| 40.69 | 2.22 | w |
| 42.02 | 2.15 | w |
| 43.38 | 2.08 | w |
| 45.02 | 2.01 | w |
| 55.85 | 1.64 | w |

EXAMPLE 27

A teflon beaker was charged with 100.2 g de-ionized water, 216.25 g phosphoric acid (85%), 30.00 g $KMnO_4$, and 14.54 g $Al(NO_3)_3*9H_2O$ in this sequence while stirring. Separately, the reductant was prepared; 35.87 g $KHCO_2$ was dissolved in 71.65 g de-ionized water. This solution was added dropwise to the manganese-aluminum-phosphate mixture. About 2 hours after this addition was completed, the pH was adjusted via the slow addition of a potassium hydroxide solution prepared from 145.8 g KOH (85%) and 170.3 g de-ionized water. The reaction mixture was then homogenized for about an hour with a high speed mixer. The mixture was placed in a teflon bottle and digested at 100° C. for 4 days. The solid products were isolated via filtration, washed with de-ionized water, and dried at room temperature.

Titrimetric analysis revealed an average manganese oxidation state of 2.63. Combined with the elemental analysis, an empirical formula of $K_{1.36}Mn_{1.00}Al_{0.20}P_{1.38}O_{5.73}$. Characteristic lines in the x-ray diffraction pattern are given in Table 26 below. This material was designated AlMnP-5.

TABLE 25

| 2θ | d(Å) | I |
|---|---|---|
| 8.37 | 10.56 | vs |
| 15.85 | 5.59 | w |
| 16.62 | 5.33 | w |
| 19.29 | 4.60 | w |
| 25.48 | 3.50 | w |
| 27.23 | 3.27 | m |
| 31.69 | 2.82 | m |
| 32.16 | 2.78 | m |
| 32.85 | 2.73 | w |
| 33.59 | 2.67 | w |
| 34.70 | 2.59 | w |
| 44.99 | 2.01 | w |
| 56.16 | 1.64 | w |

EXAMPLE 28

A teflon beaker was charged with 171.2 g de-ionized water, 104.7 g phosphoric acid (85%), 15.00 g $NaMnO_4*H_2O$, and 7.57 g $Fe(NO_3)_3*9 H_2O$ in this sequence with stirring. The pH was then adjusted via the addition of 26.23 g $NH_4OH$ (28% $NH_3$). Separately, the reductant solution was prepared by dissolving 11.95 g $NH_4HCO_2$ in 27.85 g de-ionized water. The formate solution was added dropwise to the reaction mixture, which was allowed to stir for another half hour after the addition was completed. The pH was adjusted again via the dropwise addition of 29.62 g $NH_4OH$ (28% $NH_3$). The reaction mixture was then homogenized for an hour with a high speed mixer. The final reaction mixture was then distributed among eight teflon-lined autoclaves and digested at autogenous pressures for periods of 2 and 4 days at temperatures of 100° C., 125° C., 170° C., and 200° C. The solid products were isolated via filtration, washed with de-ionized water, and dried at room temperature.

The product of interest resulted from a 200° C. digestion that lasted 4 days. This material was designated FeMnP-23. Titrimetric analysis revealed the average manganese oxidation state to be 2.70. Combined with the elemental analysis, this yields an empirical formula of $Na_{0.56}(NH_4)_{0.48}Mn_{1.00}Fe_{0.18}P_{1.01}P_{1.01}O_{4.67}$. Characteristic lines in the XRD pattern are given in Table 27 below.

TABLE 26

| 2θ | d(Å) | I |
|---|---|---|
| 4.71 | 18.75 | m |
| 9.42 | 9.38 | vs |
| 14.13 | 6.26 | w |
| 15.67 | 5.65 | w |
| 18.91 | 4.69 | w |
| 23.70 | 3.75 | w |
| 27.39 | 3.25 | w |
| 28.57 | 3.12 | w |
| 31.64 | 2.83 | w |
| 33.47 | 2.67 | w |
| 38.42 | 2.34 | w |
| 43.47 | 2.08 | w |

Example 29

In a teflon beaker, 7.22 g NaOH was dissolved in 321.93 g de-ionized water. This solution was stirred with a high speed mixer as 30.00 g $MnPO_4*H_2O$ was added. The reaction mixture was homogenized for an hour, divided among six teflon-lined autoclaves which were digested at temperatures of 100° C., 150° C., and 200° C. for time periods of 45 hrs and 95 hrs. The solid products were isolated via filtration, washed with de-ionized water, and dried at room temperature.

The product of interest was isolated from the 95 hr digestion at 150° C. This material was identified as MnP-4 (Examples 1, 23) by its XRD pattern. Characteristic lines in the x-ray diffraction pattern are given in Table 27 below.

TABLE 27

| 2θ | d(Å) | I |
|---|---|---|
| 11.22 | 7.89 | vs |
| 12.23 | 7.23 | w |
| 17.17 | 5.16 | w |
| 17.85 | 4.97 | w |
| 19.03 | 4.66 | w |
| 21.60 | 4.11 | w |
| 22.30 | 3.98 | w |
| 23.24 | 3.82 | w |
| 27.68 | 3.22 | w |
| 28.80 | 3.10 | w |
| 31.70 | 2.82 | w |
| 32.38 | 2.76 | w |
| 33.58 | 2.67 | w |
| 34.72 | 2.58 | w |
| 36.80 | 2.44 | w |
| 37.90 | 2.37 | w |
| 42.67 | 2.12 | w |

EXAMPLE 30

Using a high speed mixer, 30.00 g $MnPO_4 \cdot H_2O$ was suspended in 144.9 g de-ionized water in a teflon beaker. As the suspension stirred, 53.56 g CsOH (50%) was added to the mixture, which was homogenized for 2 hours. This yielded a brown-black suspension which settled immediately after stirring was removed. The mixture was re-suspended as it was distributed among six teflon-lined autoclaves. These were digested at temperatures of 100° C., 150° C., and 200° C. for periods of 54 hrs and 100 hrs. The solid products were isolated via filtration, washed with de-ionized water, and dried at room temperature.

A digestion temperature of 150° C. for a period of 54 hrs. yielded the material of interest, which was designated MnP-24. Titrimetric analysis revealed an average manganese oxidation state of 2.77. Combined with the elemental analysis, this yields an empirical formula of $Cs_{0.42}Mn_{1.00}P_{0.60}O_{3.10}$. Characteristic lines in the x-ray diffraction pattern are given in Table 28 below.

TABLE 28

| 2θ | d(Å) | I |
|---|---|---|
| 8.36 | 10.58 | vs |
| 13.21 | 6.70 | w |
| 19.07 | 4.65 | w |
| 19.43 | 4.57 | w |
| 21.66 | 4.10 | w |
| 23.12 | 3.85 | w |
| 23.90 | 3.72 | w |
| 24.46 | 3.64 | w |
| 25.26 | 3.53 | m |
| 26.15 | 3.41 | w |
| 26.94 | 3.31 | w |
| 27.57 | 3.23 | m |
| 29.04 | 3.07 | w |
| 29.96 | 2.98 | w |
| 31.17 | 2.87 | w |
| 32.16 | 2.78 | m |
| 32.68 | 2.74 | w |

TABLE 28-continued

| 2θ | d(Å) | I |
|---|---|---|
| 33.90 | 2.64 | w |
| 35.36 | 2.54 | w |
| 37.29 | 2.41 | w |
| 41.86 | 2.16 | w |
| 42.71 | 2.12 | w |

EXAMPLE 31

Ion Exchange Determination

In a typical experiment, 5–7.5 g of the material to be exchanged was placed in 500 ml of a metal nitrate solution which is 0.25 M with respect to the exchanging cation. The solid was stirred in the exchange solution for 24 hours at 60° C. The products were isolated by filtration and washed thoroughly with distilled water. The solids were characterized by x-ray diffraction and elemental analysis was used to determine the extent of the ion-exchange. The results are reported in terms of the percentage of the exchange sites occupied by the incoming cations.

TABLE 29

Ion-exchange results for MnP-4

| Exchange Cation | % Exchange MnP-4 |
|---|---|
| $Cs^+$ | 9% exchanged |
| $Mg^{2+}$ | 8% exchanged |
| $Li^+$ | 3% exchanged |
| $K^+$ | 48% exchanged |
| $Sr^{2+}$ | 21% exchanged |

EXAMPLE 32

Samples from example 25 and 26 were calcined at 450° C. for 2 hours in dry air and then tested. In addition, as synthesized samples from examples 25 and 26 were treated with alkali as follows. A portion of each sample was placed into a beaker and alkali metal nitrate solution having a concentration to give 2 alkali: Mn was added. The mixture was slurried transferred to a rotary steam evaporator where it was rolled at room temperature and then steam was applied to dry the solid. The dried composition was heated to 900° C. for 5 hours in flowing dry air to give a modified manganese phosphate catalyst.

Samples of each of the four catalysts described above were tested either in a micro-reactor (MR) or a laboratory pilot plan (PP). Both tests used 20–60 mesh catalyst particles in a fixed bed downflow configuration. For the MR test, a feed of isobutene and oxygen was used at a ratio of 3.4:1, while in the PP test the ratio was 4.3:1. The WHSV for the MR was 6.2 $hr^{-1}$ and for the PP it was 4 to 6 $hr^{-1}$. The reactor was heated and measurement tested starting at 350° C. and at 50° C. increments up to 600° C. The results of these tests are shown in Table 30.

TABLE 30

| | MnP-5 Ex. 26 | MnP-5 + 2 KNO$_3$ | MnP-4 Ex. 25 | MnP-4 + 2 NaNO$_3$ |
|---|---|---|---|---|
| Test | MR | PP | MR | PP |
| Loading | 0.2 g | 3.0 g | 0.11 g | 4.5 g |
| Temp | 553° C. | 532° C. | 550° C. | 545° C. |
| WHSV (hr$^{-1}$) | 6.2 | 6 | 6.2 | 4 |
| i-C$_4^-$ conversion | 11.2% | 8.2% | 5.5% | 6.9% |
| 2,5-DMH Selectivity | 13.3% | 31.4% | 15.6% | 30.0% |
| C$_8$ isomers Selectivity | 7.4% | 6.9% | 9.5% | 1.9% |
| CO$_x$ Selectivity | 47.5% | 50.6% | 31.0% | 59.2% |
| Oxygen Conversion | 100% | 96% | 45.8% | 96% |

EXAMPLE 33

Samples from examples 18 (MnP-16), 25 (MnP-4) and 26 (MnP-5) were tested for oxidative dehydrogenation using a propane pulse test. Each sample was calcined at 450° C. and then 0.1–0.5 g of 40–60 mesh granules were placed in a ¼ stainless steel tube and sandwiched between two small plugs of quartz wool. The catalysts were tested at temperatures from 400° C. to 600° C. in 50° C. increments using 3 pulses at each temperature point.

The propane pulse size was 25 μL at atmospheric pressure and was swept over the sample at a room temperature rate of approximately 25 cc/min. Conversion and selectivity were determined by GC methods. Propane conversions and normalized product selectivities from the pulse testing (after the third pulse at each temperature) are presented in Table 31.

TABLE 31

| Sample Temp. | C$_3$ Conv. | Acrolein | C$_3$H$_6$ | C$_2$H$_6$ | C$_2$H$_4$ | CH$_4$ | CO | CO$_2$ |
|---|---|---|---|---|---|---|---|---|
| | | | Product Selectivities | | | | | |
| MnP-16 450° C. | 4.7% | 0.4% | 13.4% | 0.1% | 14.5% | 0 | 17.0% | 54.5% |
| MnP-16 500° C. | 4.4% | 0 | 11.9% | 0.6% | 29.6% | 9.3% | 16.8% | 31.8% |
| MnP-16 550° C. | 3.5% | 0 | 26.0% | 1.7% | 36.0% | 21.3% | 8.8% | 6.2% |
| MnP-16 600° C. | 1.0% | 0 | 36.7% | 0.9% | 34.8% | 27.4% | 1.9% | 0.9% |
| MnP-5 450° C. | 2.2% | 0 | 24.1% | 0 | 10.5% | 0 | 18.1% | 47.3% |
| MnP-5 500° C. | 3.5% | 0 | 15.1% | 0.3% | 26.2% | 8.8% | 11.1% | 38.5% |
| MnP-5 550° C. | 4.8% | 0 | 22.8% | 0.6% | 32.1% | 16.4% | 7.8% | 20.3% |
| MnP-5 600° C. | 1.4% | 0 | 34.7% | 0.2% | 31.8% | 22.5% | 4.5% | 6.3% |
| MnP-4 450° C. | 10.1% | 0.4% | 43.2% | 0 | 5.9% | 0 | 21.4% | 29.5% |
| MnP-4 500° C. | 32.9% | 0.2% | 24.3% | 0.2% | 13.4% | 2.7% | 20.9% | 38.4% |
| MnP-4 550° C. | 79.3% | 0 | 9.4% | 0.9% | 21.3% | 5.5% | 26.3% | 36.6% |
| MnP-4 600° C. | 61.9% | 0 | 17.4% | 4.0% | 36.6% | 16.7% | 16.5% | 8.7% |

The best composition for the dehydrogenation reaction is MnP-4, which gives relatively high yields of propylene and ethylene.

EXAMPLE 34

MnP-4 from example 25 was calcined at 500° C. and then 0.25 g of 40–60 mesh granules were placed in a ¼ stainless steel tube and sandwiched between two small plugs of quartz wool. The sample was tested at 450° C. using 12 feed pulses spaced at 30 minute intervals to allow for gas chromatographic analysis of the products from each pulse. The feed consisted of 50 μL pulse of 1:1.2 propane:ammonia in a He diluent being swept through the catalyst at a rate of 40 cc/min. Table 32 gives the conversions of propane, ammonia, and normalized activities to the oxidized products.

TABLE 32

Propane/Ammonia Oxidation (Ex. 25, MnP-4)

| Pulse | C$_3$ Conv % | NH$_3$ conv % | C$_3$H$_6$ sel. % | CO sel. % | CO$_2$ sel. % | N$_2$ sel. % | N$_2$O sel. % |
|---|---|---|---|---|---|---|---|
| 1 | 21 | 71 | 27 | 20 | 53 | 39 | 60 |
| 2 | 14 | 73 | 28 | 19 | 52 | 40 | 60 |
| 3 | 12 | 73 | 29 | 18 | 52 | 40 | 60 |
| 4 | 11 | 73 | 29 | 18 | 53 | 40 | 60 |
| 5 | 11 | 73 | 29 | 18 | 53 | 40 | 60 |
| 6 | 11 | 73 | 29 | 18 | 53 | 38 | 62 |
| 7 | 11 | 74 | 29 | 18 | 53 | 38 | 62 |
| 8 | 11 | 73 | 29 | 18 | 53 | 38 | 62 |
| 9 | 11 | 74 | 29 | 18 | 53 | 38 | 62 |
| 10 | 11 | 74 | 29 | 18 | 53 | 38 | 62 |
| 11 | 11 | 74 | 29 | 18 | 53 | 38 | 62 |
| 12 | 11 | 74 | 28 | 18 | 53 | 38 | 62 |

Analysis of the products did not show the presence of acrylonitrile, acrolein, acetonitrile or HCN. It is noted that more N$_2$O than N$_2$ was formed. N$_2$O is a selective oxidant for organic compounds and thus a valuable product.

We claim:

1. A process for the oxidation of hydrocarbons comprising contacting a hydrocarbon with a crystalline manganese phosphate composition in the presence of oxygen or an oxygen source under oxidation conditions to give an oxidized product, the manganese phosphate composition having an extended network and an empirical composition on an anhydrous basis expressed by an empirical formula of:

$$(A^{a+})_v(Mn^{b+})(M^{c+})_xP_yO_z$$

where A is a structure directing agent selected from the group consisting of alkali metals, alkaline earth metals (except calcium), hydronium ion, ammonium ion, organoammonium ions, silver, copper (II), zinc (II), nickel (II), mercury (II), cadmium (II), and mixtures thereof, "a" represents a weighted average valence of A and varies from about 1.0 to about 2.0, "v" is the mole ratio of A to Mn and varies from about 0.1 to about 10, "b" is the average valence of Mn and has a value of greater than 2 to 2 maximum of 3, M is a metal selected from the group consisting of Al, $Fe^{3+}$, Ga, $Sn^{4+}$, Ti, $Sb^{5+}$, Ag, Zn, Cu, Ni, Cd, and mixtures thereof, "x" is the mole ratio of M to Mn and varies from 0 to about 3.0, "c" is the weighted average valence of M and varies from about 1.0 to about 5.0, "y" is the mole ratio of P to Mn and varies from about 0.05 to about 8.0 and "z" is the mole ratio of O to Mn and has a value determined by the equation:

$$z=\frac{1}{2}((a \cdot v)+b+(x \cdot c)+(5 \cdot y)).$$

2. The process of claim 1 characterized in that the composition has a one-dimensional extended network.

3. The process of claim 1 characterized in that the composition has a two-dimensional extended network.

4. The process of claim 1 characterized in that the composition has a three-dimensional extended network.

5. The process of claim 4 characterized in that the three-dimensional extended network is a microporous network.

6. The process of claim 1 where the oxidation process is oxidative dehydrodimerization of olefins.

7. The process of claim 6 where the oxidative dehydrodimerization conditions include a temperature of about 350° C. to about 650° C., a pressure of 0 to about 1000 psig, a WHSV of about 1 to about 50 $hr^{-1}$, and an olefin:$O_2$ ratio of about 1.5:1 to about 10:1, preferably 3:1 to 8:1.

8. The process of claim 1 where the source of oxygen is air, oxygen with an inert diluent gas or lattice oxygen from the manganese phosphate composition.

9. The process of claim 8 where the oxygen source is the lattice oxygen of the manganese phosphate composition and further comprising regenerating the manganese phosphate after a portion of the available lattice oxygen is used.

10. The process of claim 6 where the olefin is isobutene.

11. The process of claim 1 where the oxidation process is oxidative dehydrogenation of paraffins to form olefins.

12. The process of claim 11 where the oxidative dehydrogenation conditions include a temperature of about 250° C. to about 650° C., a pressure of about 1 to about 45 psig, a WHSV of about 100 to about 10,000 $hr^{-1}$ and an paraffin:$O_2$ ratio of about 1:10 to about 5:1.

13. The process of claim 11 where the paraffin is selected from the group consisting of ethane, propane, butane, isobutane, pentane and mixtures thereof.

* * * * *